United States Patent
Sershon

(10) Patent No.: US 9,986,937 B2
(45) Date of Patent: Jun. 5, 2018

(54) MODULAR GROWTH CHART ASSEMBLY

(71) Applicant: Casey Sershon, Carlsbad, CA (US)

(72) Inventor: Casey Sershon, Carlsbad, CA (US)

(*) Notice: Subject to any disclaimer, the term of this patent is extended or adjusted under 35 U.S.C. 154(b) by 147 days.

(21) Appl. No.: 15/004,291

(22) Filed: Jan. 22, 2016

(65) Prior Publication Data

US 2016/0216097 A1 Jul. 28, 2016

Related U.S. Application Data

(60) Provisional application No. 62/106,671, filed on Jan. 22, 2015.

(51) Int. Cl.
*G01B 3/02* (2006.01)
*A61B 5/107* (2006.01)
*A47G 1/06* (2006.01)

(52) U.S. Cl.
CPC .......... *A61B 5/1072* (2013.01); *A47G 1/065* (2013.01)

(58) Field of Classification Search
CPC ......... A47G 1/065; G01B 3/06; G01B 5/0004
USPC .................................... 33/512, 430
See application file for complete search history.

(56) References Cited

U.S. PATENT DOCUMENTS

| | | | | |
|---|---|---|---|---|
| D136,673 S | * | 11/1943 | Reiter | D10/71 |
| 2,369,988 A | * | 2/1945 | Steckler | A61B 5/1072 33/430 |
| 4,118,868 A | * | 10/1978 | Johnson | G01B 3/06 33/458 |
| 4,495,702 A | | 1/1985 | Bergstedt | |
| 5,303,895 A | * | 4/1994 | Hart | A47G 1/168 248/475.1 |
| D390,871 S | * | 2/1998 | Whitney | D10/71 |
| 6,519,868 B1 | * | 2/2003 | Pryor | A47G 1/065 248/221.12 |
| 7,059,060 B1 | | 6/2006 | Baumgartner | |
| 7,103,983 B2 | * | 9/2006 | Lehavi | A61B 5/1072 33/493 |
| 7,155,838 B2 | * | 1/2007 | Leyden | A61B 5/1072 33/492 |
| 7,216,841 B2 | * | 5/2007 | Dodig, Jr. | A47G 1/20 248/475.1 |
| 7,475,487 B1 | * | 1/2009 | Johnson | A61B 5/1072 33/493 |
| D587,467 S | * | 3/2009 | van der Lande | D6/303 |
| 7,770,301 B1 | * | 8/2010 | Grandberry | G01B 3/004 33/494 |

(Continued)

*Primary Examiner* — Yaritza Guadalupe-McCall
(74) *Attorney, Agent, or Firm* — Coastal Patent Law Group, P.C.

(57) ABSTRACT

A modular growth chart assembly includes a growth chart module, one or more picture frame modules removably attached to a first side of the growth chart module, and at least one decorative frame module removably attached to a second side of the growth chart module opposite of the first side. The growth chart module extends along a vertical height from a bottom end to a top end. The growth chart module includes hash marks disposed along its vertical height for measuring height, for example, of a child. Photos of the child can be implemented with the picture frame modules for adapting the growth chart assembly to a particular user or child. With the modular growth chart assembly, a user may substitute the decorative frame module to adapt the growth chart assembly along with a child's changing preference or interest.

18 Claims, 5 Drawing Sheets

(56) References Cited

U.S. PATENT DOCUMENTS

| | | | |
|---|---|---|---|
| 8,151,478 B2* | 4/2012 | Kenney | A61B 5/1072 33/511 |
| 8,528,221 B2 | 9/2013 | Glock | |
| 8,869,415 B1 | 8/2014 | Haykeen | |
| 9,536,448 B1* | 1/2017 | Kordecki, Jr. | G09B 19/00 |
| 2010/0088915 A1* | 4/2010 | Neff | A61B 5/107 33/759 |
| 2010/0223799 A1* | 9/2010 | Dunham | A61B 5/1072 33/512 |
| 2012/0144686 A1* | 6/2012 | Haykeen | A61B 5/1072 33/512 |
| 2014/0190029 A1* | 7/2014 | Blakely | A61B 5/1072 33/512 |
| 2014/0198623 A1* | 7/2014 | Hill | G04G 13/026 368/10 |
| 2016/0216097 A1* | 7/2016 | Sershon | A47G 1/065 |

* cited by examiner

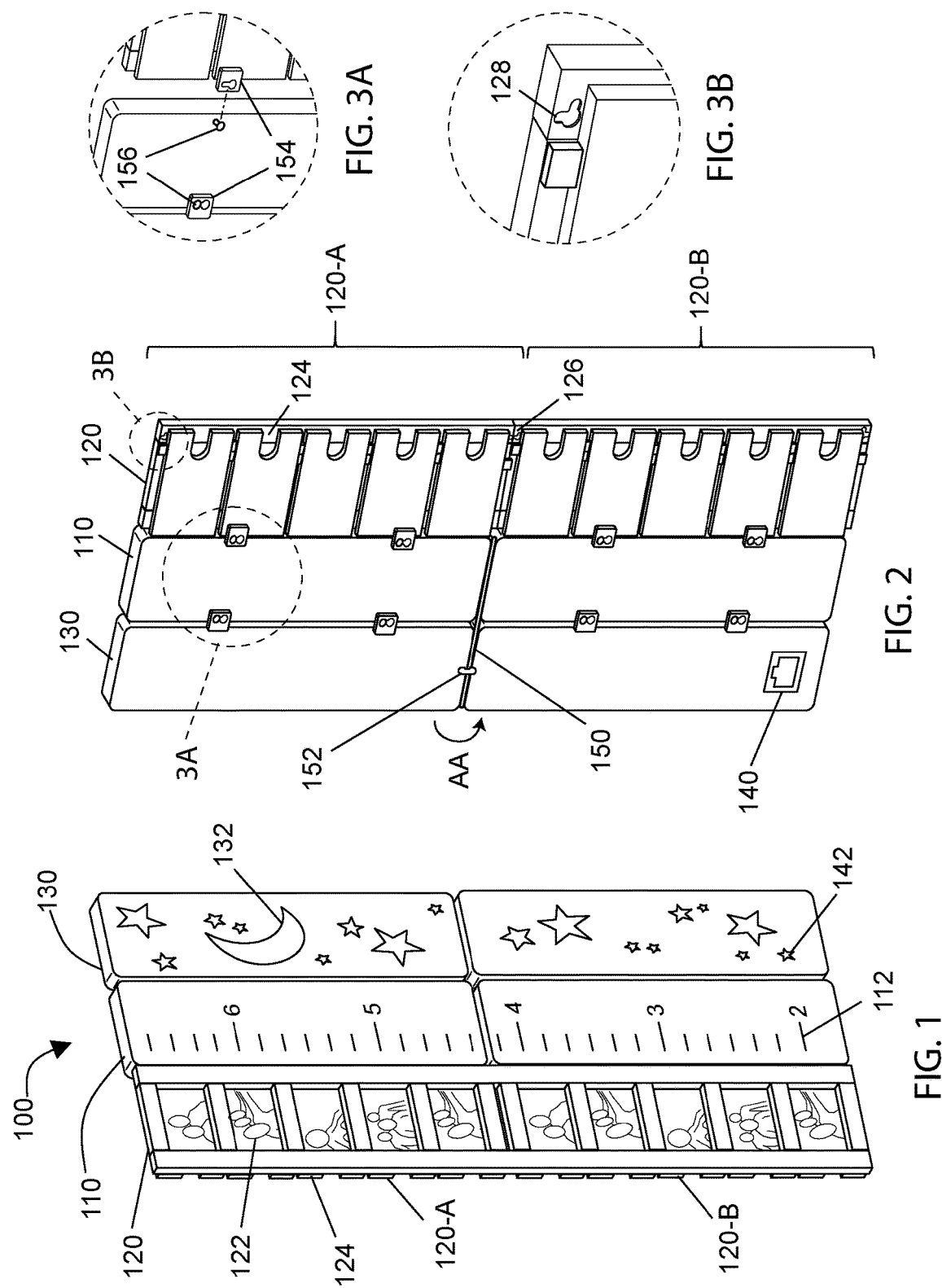

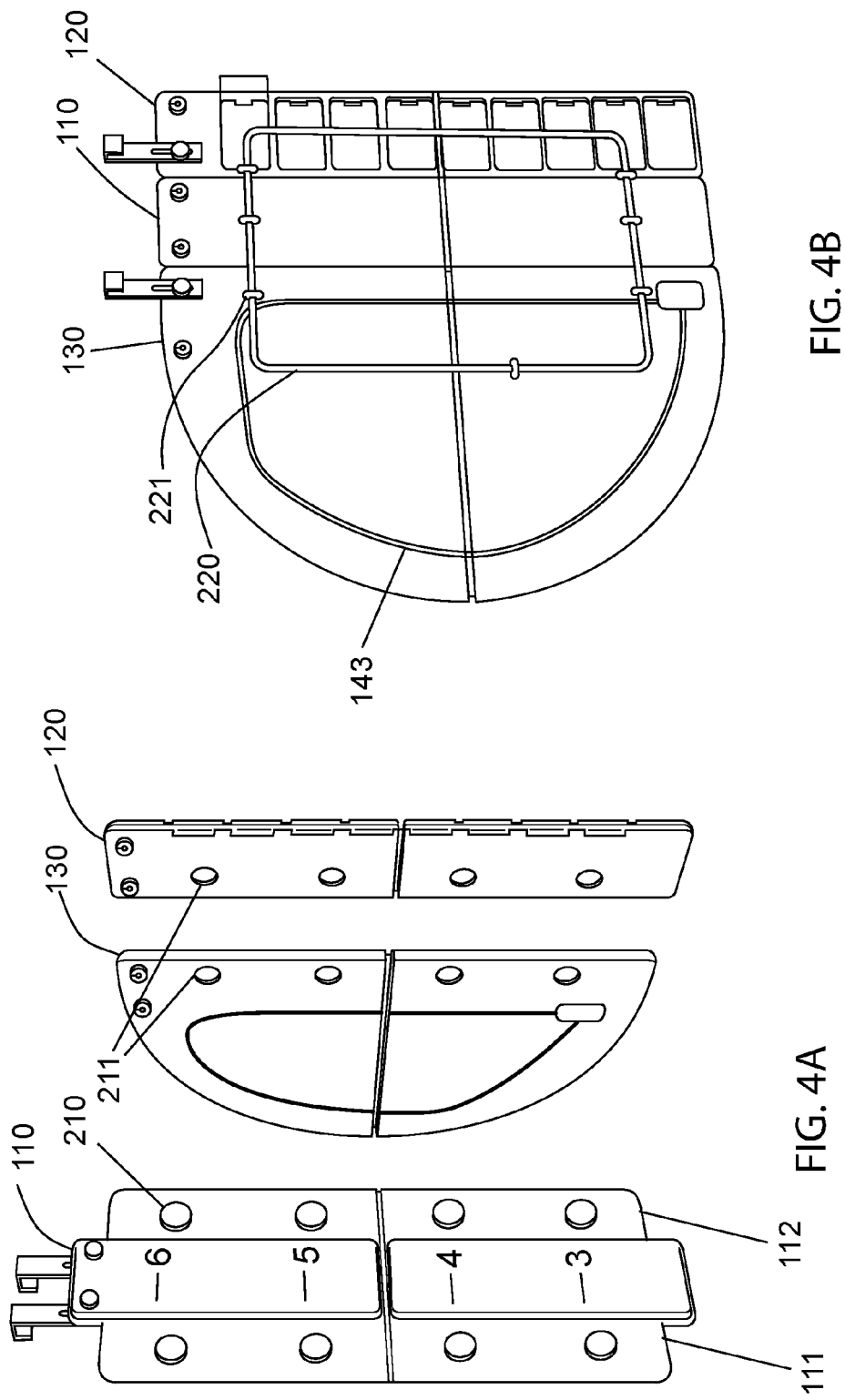

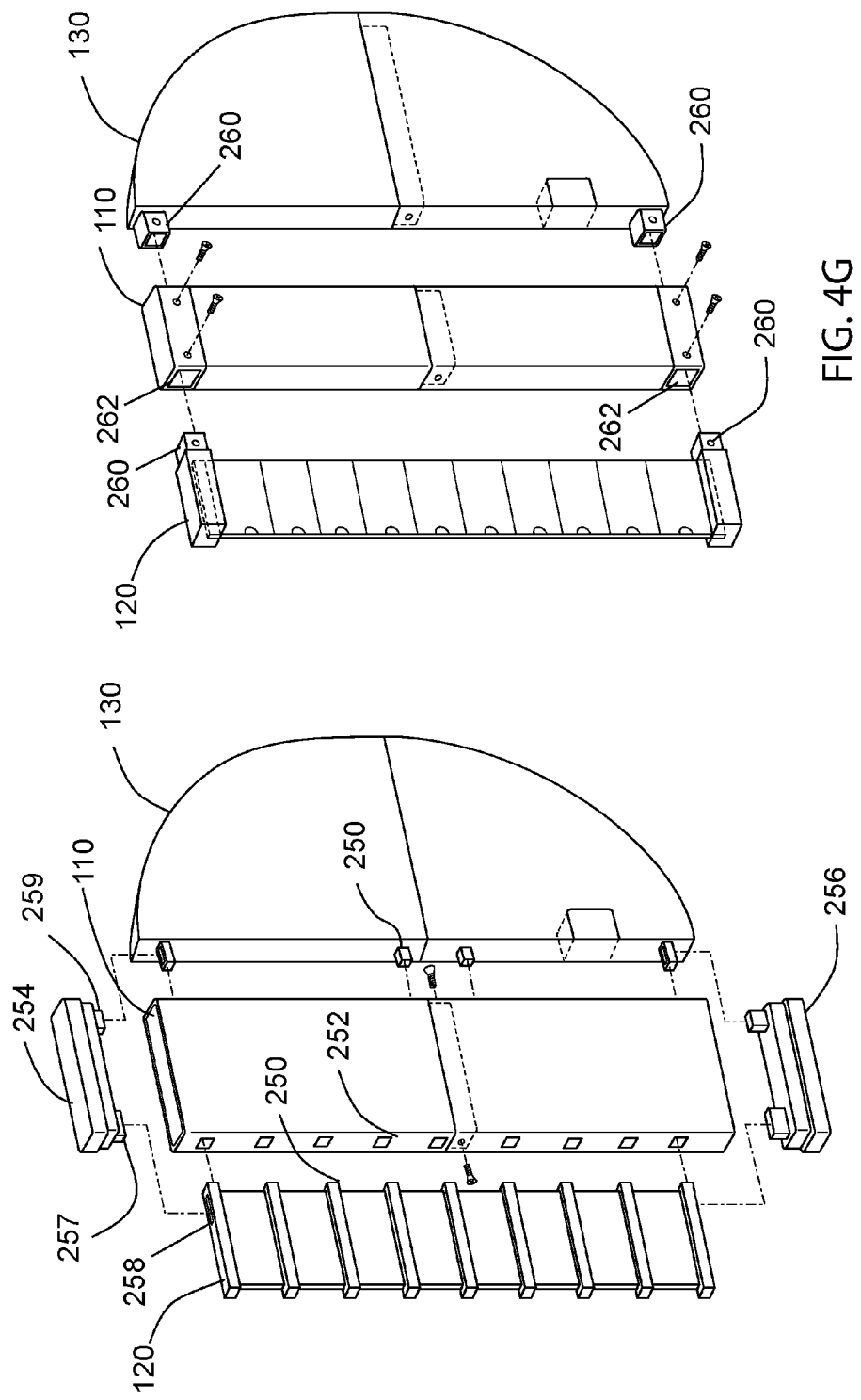

MODULAR GROWTH CHART ASSEMBLY

CROSS-REFERENCE TO RELATED APPLICATIONS

The present application claims benefit of priority with U.S. Provisional Application No. 62/106,671, filed Jan. 22, 2015, which is hereby incorporated by reference.

BACKGROUND

Field of the Invention

The claimed invention relates to devices for measuring height of a child; and more particularly, to a modular growth chart assembly being reconfigurable using picture frame and decorative modules configured to attach with the growth chart for varying a theme of the growth chart over a period of time to match the interest of a user.

Description of the Related Art

In many families, parents measure the heights of their children by making marks on walls or in doorways. Such markings often not only are aesthetically displeasing, but may also cause damages to the home. In addition, such markings are also lost when the walls are painted over, or when the families move. There are currently available a number of child height measurement boards that remain aesthetically displeasing, or lack interesting features.

Moreover, the currently available child height measurement boards, or "growth charts", provide only a single function for measuring. Thus, there is a present need and desire for devices for measuring height of a child that are aesthetically pleasing, have multiple functional purposes, and also can be moved and reconfigured with the child.

SUMMARY

A modular growth chart assembly includes a growth chart module, one or more picture frame modules removably attached to a first side of the growth chart module, and at least one decorative frame module removably attached to the a second side of the growth chart module opposite of the first side. The growth chart module extends along a vertical height from a bottom end to a top end. The growth chart module includes hash marks disposed along its vertical height for measuring height, for example, of a child. Photos of the child can be implemented with the picture frame modules for adapting the growth chart assembly to a particular user or child. With the modular growth chart assembly, a user may substitute the decorative frame module to adapt the growth chart assembly along with a child's changing preference or interest.

BRIEF DESCRIPTION OF THE DRAWINGS

The claimed invention can be further understood upon a thorough review of the following detailed description in conjunction with the appended drawings, wherein:

FIG. 1 shows a perspective front view of a growth chart assembly in accordance with a first illustrated embodiment;

FIG. 2 shows a perspective rear view of the growth chart assembly in accordance with the first illustrated embodiment of FIG. 1;

FIG. 3A shows perspective view of an attachment feature of the first illustrated embodiment;

FIG. 3B shows a perspective view of a hanging feature of the first illustrated embodiment;

FIG. 4A shows a perspective front view of a growth chart assembly using Velcro or magnetic attachment features in accordance with a second illustrated embodiment;

FIG. 4B shows a perspective rear view of the growth chart assembly using an annular tube support in accordance with the second illustrated embodiment;

FIG. 4F shows a perspective front view of a growth chart assembly using an alternative attachment feature for assembly and having caps in accordance with a fifth illustrated embodiment;

FIG. 4G shows a perspective front view of a growth chart assembly using another alternative attachment feature for assembly in accordance with a sixth illustrated embodiment.

DETAILED DESCRIPTION

Figure 4E:
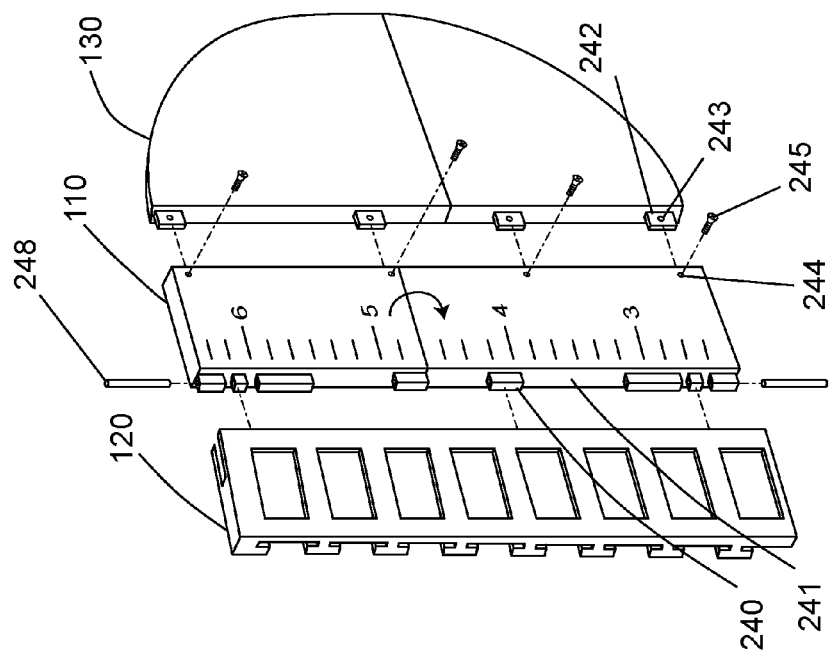
FIG. 4E shows a perspective front view of a growth chart assembly implementing an alternative attachment feature in accordance with a fourth illustrated embodiment.

In the following description, for purposes of explanation and not limitation, details and descriptions are set forth in order to provide a thorough understanding of the claimed invention. However, it will be apparent to those skilled in the art that the claimed invention may be practiced in other embodiments that depart from these details and descriptions without departing from the spirit and scope of the invention. Certain embodiments will be described below with reference to the drawings wherein illustrative features are denoted by reference numerals.

In the following description and in the figures, like elements are identified with like reference numerals. The use of "e.g.," "etc.," and "or" indicates non-exclusive alternatives without limitation, unless otherwise noted. The use of "including" or "includes" means "including, but not limited to," or "includes, but not limited to," unless otherwise noted.

A modular growth chart assembly is disclosed. The modular growth chart assembly includes a growth chart module, one or more picture frame modules removably attached to a first side of the growth chart module, and at least one decorative frame module removably attached to opposite second side of the growth chart module opposite the first side. The growth chart module extends along a vertical height from a bottom end to a top end. The growth chart module includes hash marks disposed along its vertical height for measuring a height, for example, of a child.

In some embodiments, each picture frame module includes multiple picture slots or holders for receiving individual pictures. The picture frame modules may be removed from the modular growth chart assembly and used as picture frames separately, for instance, when the child has grown and the growth chart is no longer desired.

In some embodiments, the decorative frame module includes lighting components on its back side. The lighting components illuminate light through one or more decorative features on the decorative frame module to provide backlighting. Light-emitting diode (LED) lighting, or any suitable lighting, may be used for the lighting components. A light control switch can be accessible at the front of the decorative frame module to control a state of the lighting components, for example "On", "Off", "Dimmed" or "Blink". Using the light control switch, the lighting components may be turned on, off, or may be dimmed (if using dimmable lighting components) or configured to blink or otherwise change a state of the lighting components in conjunction with a control sequence or algorithm using memory and a controller.

The decorative frame may further include one or more accessories embedded therein or affixed thereto, the accessories may include: hooks and other hanging elements for hanging hats and clothing or other items, small cubbies or shelves for storing or displaying items, a blackboard or whiteboard for writing or drawing, a corkboard for tacking items or notes, a calendar for planning events, clips, pockets, Velcro, a pocket for dry erase pens and/eraser, or other attachments or accessories that would be known to this having skill in the art. In this regard, while being primarily decorative, the decorative frame may further serve one or more functional purposes by implementing one or more functional accessory features.

Each module (e.g., growth chart module, picture frame module, decorative frame module) of the modular growth chart assembly includes hanging features disposed about a rear side thereof. The hanging features allow the modular growth chart assembly to be hung on a wall, or on a door. The modular growth chart assembly may be hung as a single assembly unit, for example, including a growth chart module, one or more picture frame modules, and at least one decorative frame module. One or more modules of the modular growth chart assembly may also be separated and hung individually.

Now turning to the drawings, FIGS. 1 and 2 illustrate respectively the front and rear perspective views of an exemplary modular growth chart assembly 100 including a growth chart module 110, a picture frame module 120 removably attached to a first side of the growth chart module 110, and a decorative frame module 130 removably attached to opposite second side of the growth chart module 110 opposite the first side. The growth chart module 110 includes hash marks 112 disposed along its vertical height. The hash marks provide an easy and accurate way to keep a record, for example, of the height of a child. The hash marks 112 may be labeled in the manner that conventional rulers are labeled, for example, in American measurement system (e.g., inches, feet), or in metric system (e.g., centimeters, meters), or both. In some embodiments, the hash marks 112 may range from a two-foot label at the bottom end to a six-foot label at the top end. In this example, a user will install the growth chart module 110 so that the two-foot label will be measured two feet from the ground. Other ranges of labeling may also be used. While the above example describes a two-foot installation, it should be recognized that the growth chart may be installed from ground level, and up to several feet from the ground, though, in a preferred embodiment the growth chart will be installed from two-feet above ground level.

The one or more picture frame modules 120 may include picture holders or "picture displays" 122. In some embodiments, each picture display 122 includes a vertical aperture 124 through which a photograph may be inserted. In an exemplary use of the modular growth chart assembly 100, a user may fill the picture frame module 120 with the photos of a child's current year of life, or the user may start with year one and add photos along with the growth chart module 110 for each successive month or year. This way there will be a visual representation of the child's growth that coincides with the hash marks 112 tracking on the growth chart module 110. Alternatively, any photos of the user's interest may be implemented with the picture frame modules.

In the exemplary embodiment shown in FIGS. 1 and 2, the growth chart assembly 100 comprises two picture frame modules 120-A and 120-B. The two picture frame modules 120-A and 120-B are positioned vertically one on top of another, respectively. In some embodiments, the picture frame modules 120-A and 120-B may be fastened together using any fastening attachment known in the art. In other embodiments, the picture frame modules are independently fixed to the growth chart module to form the assembly.

In some embodiments, more than one picture frame module 120 may be attached to the growth chart module 110. It is noted that when more than one picture frame module 120 is attached to the growth chart module 110, all picture frame modules 120 can be attached to a common side of the growth chart module 110, for example, the first side.

The decorative frame module 130 is removably attached to the growth chart module 110 on the second side of the growth chart module 110, opposite the first side from where the one or more picture frame modules 120 are attached. The decorative frame module 130 may include decorative features 132. In some embodiments, one or more decorative features 132 may be fabricated with material that allows light to shine through, for example a translucent material including a thin plastic sheet or other translucent material. In other embodiment, one or more portions of the decorative frame module may be transparent, or alternatively one or more portions of the lighting components may protrude through a surface of the decorative frame module. In these embodiments, the decorative frame module 130 includes lighting components (see, e.g., lighting 143 in FIG. 4B) disposed at a rear side of the decorative frame module 130. The lighting components may be powered by battery installed in battery compartment 140. Alternatively, the assembly can be configured to plug into a conventional 110 v power outlet or similar electrical source. The lighting components may be controlled by a lighting control 142 (or switch) disposed in the front of the decorative frame module 130. The lighting components may be turned on, off, or may be dimmed (if using dimmable lighting components). The lighting components may illuminate through one or more decorative features 132 causing the decorative frame module 130 to glow in the dark and accentuate key features of the design of the decorative frame module 130. In these embodiments, the growth chart assembly 100 may also be used as a night light. LED lighting, or any suitable lighting, may be used for the lighting components.

In some embodiments, more than one decorative frame module 130 may be attached to the growth chart module 110. It is noted that when more than one decorative frame modules 130 are attached to the growth chart module 110, all decorative frame modules 130 can be attached to a common side of the growth chart module 110. Alternatively, one or more decorative frame modules can be configured to attach with a first side of the growth chart module, and one or more additional decorative frame modules can be attached to a second side of the growth chart module. Similarly, the picture frame modules can be attached to the growth chart module at a common side, or at multiple sides thereof.

In another exemplary use of the growth chart assembly 100, a user may remove a decorative frame module 130 from the growth chart module 110 and attach a different decorative frame module 130 to reconfigure the growth chart assembly. The user may substitute the decorative frame module 130 to adapt the growth chart assembly 100 along with a child's changing preference or interest. For example, in year one the decorative frame module 130 may have decorative features of, or be in the shape of, for example, farm animals, in year two the features or shape may change to, for example, trains, year three may be a cartoon figure, year four may change to another cartoon or comic character, year five a superhero, year six another fictional character, year seven a professional sports team, and so on. The decorative frame module 130 may include licensed properties, for example, a cartoon, comic, or superhero character, or a sports team, an athlete, and the like.

In some embodiments, the growth chart module 110 and the decorative frame module 130 may be folded vertically along a horizontal folding line 150, as shown with directional line AA.

In some embodiments, the structure of the growth chart module 110 and the decorative frame module 130 may be fabricated with vacuum-formed plastic which allows them to be foldable. In these embodiments, when the growth chart module 110 and the decorative frame module 130 are in an open (not folded) position, one or more hinges 152 may be installed in the back of the growth chart module 110 and picture frame module 120 along the folding line 150 to securely hold the growth chart module 110 and the decorative frame module 130 in the open position. Alternatively, one or more of the growth chart module, picture frame module and decorative frame module may include a single monolithic piece formed with a thermoforming or vacuum forming process, such that a horizontal folding line may include a thin junction between a top portion and a bottom portion of the monolithic piece(s). The folding capability provides lower shipping rates and improved storage of the assembly components when not in use.

In some embodiments, one or more modules of the growth chart assembly 100 may have a double wall (or layered) structure. In these embodiments, the panels (or walls) may include a top shell and a bottom shell, and may be combined using an adhesive such that one is securely attached over another, respectively. As noted herein, each panel may be fabricated with vacuum-formed plastic. The front panel may include a thinner wall than the back panel. The thinner front panel allows for better three-dimensional molding. The thicker back panel provides structure rigidity. In the embodiments using a double wall structure, the lighting components of the decorative frame module 130 may be disposed in between the front and the back panels.

In other embodiments, the picture frame module 120 may be fabricated with injection molded parts.

Turning to FIG. 3A, in some embodiments, the picture frame module 120 and the decorative frame module 130 may be attached to the growth chart module 110 using keyhole fittings 154 and standoffs 156 as attachment features.

Turning to FIG. 3B, in some embodiments, the hanging feature 128 in the back of the picture frame module 120 allows the picture frame module 120, when detached from the growth chart assembly 100, to be hung on a wall, either horizontally or vertically.

Other exemplary embodiments for connecting the picture frame module 120 and the decorative frame module 130 to the growth chart module 110, herein the "attachment features", are shown in FIGS. 4(A-G).

FIG. 4A shows the growth chart module 110 having flanges 111 and 112 including Velcro or magnetic connectors 210 for connecting with respective Velcro or magnetic connectors 211 in the back of the picture frame module 120 and the decorative frame module 130.

FIG. 4B illustrates an annular tube support 220 and locks 221 being used to connect the picture frame module 120 and the decorative frame module 130 to the growth chart module 110. In this illustrated embodiment, the annular tube support 220 may be adjustable, for example, using a telescoping feature, to match the width of the modules of the growth chart assembly 100. The annular tube support 220 may also be adjusted to a smaller size for storage. In some embodiments, the annular tube support 220 may be fabricated with aluminum. The locks 221 may be snap-locking connectors, or any other connectors that would be appreciated by those with skill in the art.

Figure 4D:
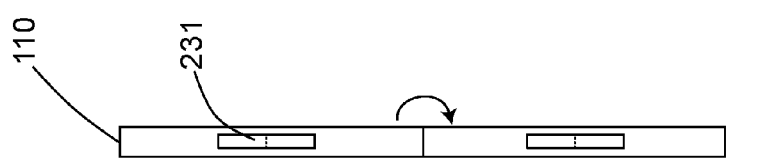
FIG. 4D shows a side view of the growth chart module having slots for receiving and locking with the respective hook attachment features of the decorative frame module for assembling the modular growth chart assembly in accordance with the third illustrated embodiment.
Figure 4C:
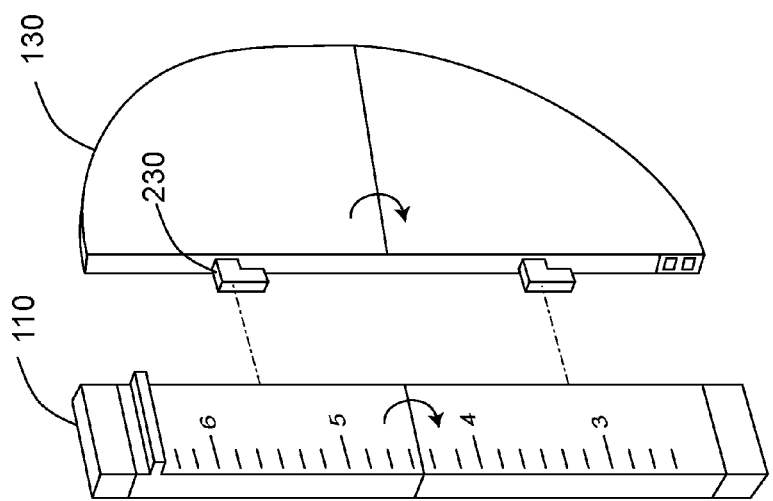
FIG. 4C shows a perspective front view of a growth chart assembly having a decorative frame module with hook attachment features in accordance with a third illustrated embodiment.

FIGS. 4C and 4D illustrate another exemplary embodiment of attachment features for connecting the picture frame module 120 (not shown) and the decorative frame module 130 to the growth chart module 110. FIG. 4D shows a side view of the growth chart module 110 of this illustrated embodiment. The growth chart module 110 includes vertically elongated apertures (slots) 231 for receiving the hook attachment features 230 disposed on the side of the picture frame module 120 (not shown) and the decorative frame module 130. The hook attachment features 230 are inserted into the top opening portion of the slots 231, then pushed down to lock the picture frame module 120 (not shown) and the decorative frame module 130 to the growth chart module 110. In this embodiment, it should be noted that picture frame modules are optional, and the growth chart assembly may comprise only a growth chart module and a decorative frame module. However, for illustrative purposes, the attachment features, including hooks and slots, may be similarly implemented into picture frame and other modules of the invention.

Any snap-fit design known by those having skill in the art may be similarly implemented for joining two or more modules of the modular growth chart assembly.

FIG. 4E further illustrates another exemplary embodiment of attachment features for connecting the picture frame module 120 and the decorative frame module 130 to the growth chart module 110. In this illustrated embodiment, the box joint method may be used, as illustrated with the picture frame module 120 and the left side of the growth chart module 110. The right side of the picture frame module 120 and the left side of the growth chart module 110 includes fingers 240 and notches 241. Each notch 241 on the growth chart module 110 receives a corresponding finger 240 on the picture frame module 120, and vice versa. A top and a bottom threaded pins 248 may be used to secure the picture frame module 120 to the growth chart module 110.

Also in this illustration, the left side of the decorative frame module 130 may include flanges 242 each having a circular aperture 243. The right side of the growth chart module 110 may then include elongated corresponding apertures for receiving the flanges 242 on the decorative frame module 130. The growth chart module 110 may include corresponding apertures 244 aligned with the apertures 243 when the flanges 242 are inserted into the growth chart module 110. Screws 245 are then used to secure the decorative frame module 130 to the growth chart module 110. Although two different attachment methods are illustrated in the exemplary embodiment of FIG. 4E, one or both of these methods may be used to attach both the picture frame module 120 and the decorative frame module 130 to the growth chart module 110.

FIG. 4F illustrates another exemplary embodiment of attachment features for connecting the picture frame module 120 and the decorative frame module 130 to the growth chart module 110. In this, the picture frame module 120 and the decorative frame module 130 include one or more fingers 250 which may be inserted into corresponding apertures 252 on the sides of the growth chart module 110. The growth chart module 110 is hollow at least at the top and bottom for receiving top cap 254 and bottom cap 256. The top and bottom ends of the picture frame module 120 include apertures 258 for receiving fingers 257 of the top cap 254 and bottom cap 256. Similarly, the top and bottom fingers 250 of the decorative frame module 130 include apertures for receiving fingers 259 of the top cap 254 and bottom cap 256. Attachment feature, such as bolt or snap-lock, may be used to further secure the picture frame module 120 and the decorative frame module 130 to the growth chart module 110.

FIG. 4G illustrates another exemplary embodiment of attachment features for connecting the picture frame module 120 and the decorative frame module 130 to the growth chart module 110. In this illustrated embodiment, the picture frame module 120 and the decorative frame module 130 include top and bottom fingers 260 which may be inserted into corresponding apertures 262 at the top and bottom of the growth chart module 110. Attachment feature, such as screws or snap-lock, may be used to further secure the picture frame module 120 and the decorative frame module 130 to the growth chart module 110.

In some other embodiments, the picture frame module 120 and the decorative frame module 130 may be attached to the growth chart module 110 using plates and screws. Slide-in clips may also be used. In this embodiment, a male end of the clip disposed on one module is slid into a female end of the clip disposed on another module for attaching the two modules. Other fastening devices may also be used.

In some embodiments, each module of the growth chart assembly 100 may each be made of two separate top and bottom sections. In these embodiments, various attachment features may be used to couple the top and bottom sections together. For example, living hinges may be used. The hinges may also allow the module to fold vertically. In other examples, as shown in FIGS. 4F and 4G, elongated fingers extending along the width of a section and corresponding apertures on the corresponding section may be used to snap-lock the two sections together.

Figure 5:
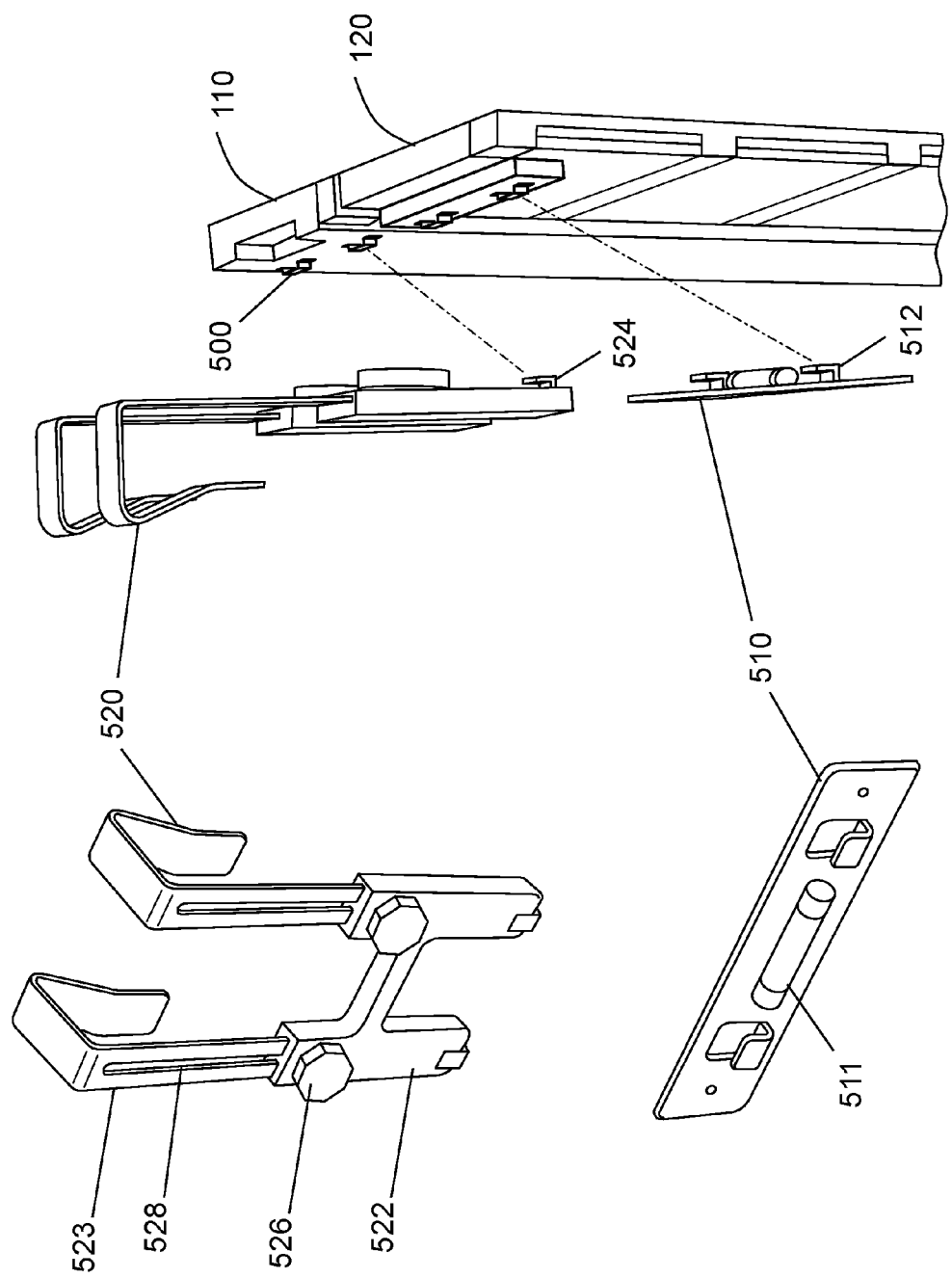
FIG. 5 shows exemplary embodiments of hanging mechanisms for the growth chart assembly in accordance with any of the illustrated embodiments.

Turning to FIG. 5, exemplary embodiments of mechanisms for hanging the growth chart assembly 100 are shown. In some embodiments, each module of the growth chart assembly 100 may include one or more frame back hangers 500 in the back and near the top edge of the module. The frame back hangers 500 receive hooks 512 of a leveling bracket 510, or receive hooks 524 of door hanger assembly 520.

In an exemplary operation, one or more leveling brackets 510 each having leveling vial 511 may be attached horizontally to a wall at a desired height. The growth chart assembly 100 will then be hung on the leveling bracket(s) by hooking the frame back hangers 500 in the back of the growth chart assembly 100 to the hooks 512 of leveling bracket 510. While illustrated with an integrated leveling vial, the brackets may not necessarily include a leveling vial, and such a leveling vial is optional though preferred for simplicity in hanging the growth chart assembly.

In another exemplary operation, the door hanger assembly 520 is configured to be hung on a door. The vertical length of the door hanger assembly 520 may be adjusted by sliding the hooks 523 up or down along a door hanger base 522 via guide channels 528. At the desired vertical length, knobs 526 are tightened. The growth chart assembly 100 will then be hung on the door hanger assembly 520 by hooking the frame back hangers 500 in the back of the growth chart assembly 100 to the hooks 524 of the door hanger assembly 520.

Turning back to FIGS. 4A and 4B, in some embodiments, individual adjustable door hangers may be attached to the back of one or more modules of the growth chart assembly 100. Each adjustable door hanger may be attached to a module using hand screws, or hand knobs with threaded studs. The adjustable door hangers may include a hanger body, and a channel extending along a vertical portion of the hanger body, as shown.

In some embodiments, the adjustable door hanger may have a plurality of holes disposed along its vertical body, or alternatively, the channels can be implemented as discussed above. The hanger may then be inserted into an aperture at the top of a module. A pin lock is then inserted into a hole in the back of the module, through one of the holes along the vertical body of door hanger. Alternatively, the hanger may simply be attached by a screw or other attachment feature.

In some embodiments, one or more modules of the growth chart assembly 100 may include a vacuum formed pocket for storing markers and the like. The vacuum formed pocket can be formed into a module during the vacuum-forming process. Alternatively, the pocket can be attached post-process. The pocket is generally attached along a perimeter of the assembly, though may be placed anywhere, and preferably the pocket is positioned on an outward facing surface of the growth chart assembly.

In other variations, the picture frame modules can be individually configured to display one or more pictures in each of the one or more picture slots of the respective picture module. For example, in some embodiments, a digital picture can be produced using a liquid crystal or similar display. In other embodiments, one or more printed pictures can be fitted and displayed in each picture slot, i.e. a collage of pictures can be inserted in a picture slot of the respective picture frame module. While a picture slot (otherwise herein termed a "picture holder" or "display") may display a single static picture (such as in the case of a printed picture resident in the picture holder), the picture slot may further include an LCD screen for presenting multiple pictures. In addition, the picture frame module or other component herein may be fitted with a controller configured to communicate with a database via a communication cable or via a wireless connection for receiving digital pictures for presenting in the picture display(s). Using conventional algorithms, the picture display(s) of the picture frame module may stream or otherwise present a series of pictures, in order in in random succession, according to a folder containing digital pictures, wherein the folder can be stored in memory with the modular growth chart assembly, or digital pictures communicated wirelessly via an internet or similar wireless communication connection (ex: Bluetooth or WiFi connection).

Thus, in the various embodiments, the modular growth chart assembly is adaptable to a child or user's interest at a particular time, and modules are interchangeable to reconfigure the growth chart assembly to the child or user's particular interest. The modular growth chart assembly as described herein allows a user to keep information while manipulating the appearance over time with content that is relative to the child's age and interests.

Now, although particular features and embodiments have been described in an effort to enable those with skill in the art to make and use the claimed invention, it should be understood that several variations, alterations or substitutions can be achieved to fabricate and operate the growth chart assembly. Nothing in this description shall be construed as limiting the spirit and scope of the invention as set forth in the appended claims, below.

What is claimed is:

1. A modular growth chart assembly, comprising:
a growth chart module extending along a vertical height from a bottom end to a top end and having a first side and a second side opposite the first side, the growth chart module including a plurality of hash marks disposed along the vertical height;
one or more picture frame modules configured to attach to the growth chart module at the first side, each of the picture frame modules being configured to display one or more pictures in each of one or more picture displays of the picture frame module; and
at least one decorative frame module configured to attach to the growth chart module at the second side, the decorative frame module including an ornamented surface,
wherein said picture displays include a liquid crystal display (LCD) screen for presenting digital pictures.

2. The modular growth chart assembly of claim 1, wherein each of the one or more picture frame modules comprises a plurality of picture displays for receiving and presenting individual pictures.

3. The modular growth chart assembly of claim 1, wherein the at least one decorative frame module is fabricated with a translucent material.

4. The modular growth chart assembly of claim 1, wherein one or more of the growth chart module, the decorative frame module and the picture frame module is configured for folding about a horizontal folding line.

5. The modular growth chart assembly of claim 1, wherein one or more of the growth chart module and the at least one decorative frame module includes multiple layers.

6. The modular growth chart assembly of claim 1, wherein the one or more picture frame modules and the at least one decorative frame module are configured for attachment with the growth chart module by one or more attachment features.

7. The modular growth chart assembly of claim 1, wherein the attachment features include one or more of the group consisting of: keyhole fittings and corresponding standoffs, Velcro, and magnetic attachments.

8. The modular growth chart assembly of claim 1, wherein the one or more picture frame modules and the at least one decorative frame module are attached to the growth chart module using an annular tube support and corresponding locks.

9. The modular growth chart assembly of claim 1, wherein the one or more picture frame modules and the at least one decorative frame module are attached to the growth chart module using hooks and corresponding slots.

10. The modular growth chart assembly of claim 1, wherein the one or more picture frame modules and the at least one decorative frame module are attached to the growth chart module using a box joint method.

11. The modular growth chart assembly of claim 1, wherein the one or more picture frame modules and the at least one decorative frame module are attached to the growth chart module using a top cap and a bottom cap.

12. The modular growth chart assembly of claim 1, wherein the assembly further comprises one or more brackets for hanging one of: the growth chart module, the one or more picture frame modules, or the at least one decorative frame module, or a combination thereof.

13. The modular growth chart assembly of claim 12, said brackets including one or more leveling brackets, wherein said leveling brackets comprise a built-in leveling vial.

14. The modular growth chart assembly of claim 1, wherein the assembly further comprises one or more door hanger assemblies for hanging the modular growth chart assembly on a door.

15. The modular growth chart assembly of claim 14, wherein each of the one or more door hanger assemblies is vertically adjustable.

16. A modular growth chart assembly, comprising:
a growth chart module extending along a vertical height from a bottom end to a top end and having a first side and a second side opposite the first side, the growth chart module including a plurality of hash marks disposed along the vertical height;
one or more picture frame modules configured to attach to the growth chart module at the first side, each of the picture frame modules being configured to display one or more pictures in each of one or more picture displays of the picture frame module; and
at least one decorative frame module configured to attach to the growth chart module at the second side, the decorative frame module including an ornamented surface, wherein the at least one decorative frame module comprises one or more lighting components.

17. The modular growth chart assembly of claim 16, wherein the one or more lighting components are disposed about a rear side of the at least one decorative frame module.

18. A modular growth chart assembly, comprising:
a foldable growth chart module extending along a vertical height from a bottom end to a top end, the growth chart module including a plurality of hash marks disposed along the vertical height;
one or more picture frame modules configured to attach to the growth chart module at a first side thereof, wherein each of the one or more picture frame modules further comprises one or more picture displays;
at least one foldable decorative frame module configured to attach to the growth chart module at a second side thereof opposite the first side, wherein the at least one decorative frame module comprises a light control switch and one or more lighting components for controlling a lighting state of the assembly; and
wherein the modular growth chart assembly is configured to be hung on a wall or on a door.

* * * * *